(12) United States Patent
Mahieu et al.

(10) Patent No.: US 6,479,044 B1
(45) Date of Patent: Nov. 12, 2002

(54) ANTIBACTERIAL SOLUTION

(75) Inventors: Marianne Mahieu, Ayeneux (BE); Germaine Zocchi, Villers-Aux-Tours (BE); Yasmine Cartiaux, Saint Nicolas (BE)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/874,610

(22) Filed: Jun. 5, 2001

(51) Int. Cl.[7] .................. A61K 31/74; A61K 9/00; A01N 25/00

(52) U.S. Cl. .............. 424/78.03; 424/405; 424/400

(58) Field of Search ................. 424/78.03, 65, 424/5, 67, 69, 76.1, 405, 717

(56) References Cited

U.S. PATENT DOCUMENTS 5,942,214 A * 8/1999 Lucas et al. .......... 424/65

\* cited by examiner

*Primary Examiner*—Thurman K. Page
*Assistant Examiner*—Blessing Fubara
(74) *Attorney, Agent, or Firm*—Richard E. Nanfeldt

(57) ABSTRACT

The present invention relates to an antibacterial aqueous solution comprising a complex of an anionic surfactant, a polycationic antibacterial agent and water.

2 Claims, No Drawings

ANTIBACTERIAL SOLUTION

FIELD OF THE INVENTION

The present invention relates to an aqueous antibacterial solution containing an anionic surfactant, a polycationic antibacterial agent and water, wherein the antibacterial solution has improved substantivity onto surfaces for a lasting protection against bacteria.

BACKGROUND OF THE INVENTION

Poly (hexamethylene biguanide) hydrochloride has been used in the food industry as an antibacterial solution for equipment disinfection but these solutions exhibit poor substantivity in that once the bacteria has been killed on the initial treatment with the antibacterial solution, new bacteria can readily grow on the treated surface. The instant aqueous antibacterial solution of a complex of an anionic surfactant and a poly (hexamethylene biguanide) hydrochloride exhibits improved substantivity in that the treated surface is resistant to the growth of new bacteria.

Poly (hexamethylene biguanide) hydrochloride has been used in combination with a cationic surfactant such as didecyl dimethyl ammonium chloride in laundry compositions but the substantivity of these laundry compositions is inferior.

Patent applications WO99/40791 and EPO891712A1 comprises a substantive antibacterial solution containing silver ions, poly (hexamethylene biguanide) hydrochloride which is crosslinked by sodium lauryl sulfate.

Avecia Limited of England also provides poly (hexamethylene biguanide) stearate for soap bars.

SUMMARY OF THE INVENTION

The present invention relates to an aqueous antibacterial solution having improved substantivity which comprises a complex of an anionic surfactant and poly (hexamethylene biguanide) hydrochloride in suspension in water.

An objective of the present invention is to provide an antibacterial solution for the treatment of a surface containing bacteria, wherein the treated surface is resistant to further growth of new bacteria.

DETAILED DESCRIPTION OF THE INVENTION

The present invention relates to an aqueous antibacterial solution which comprises approximately by weight:

(a) a complex of 0.01% to 5.0%, more preferably 0.1% to 0.5% of an anionic surfactant and 0.01% to 2%, more preferably 0.04% to 0.2% of a cationic polymer selected from the group consisting of poly (hexamethylene biguanide) hydrochloride having the structure of:

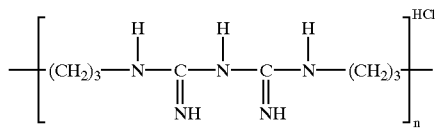

where the average n=4 to 6 and a quaternized cationic polymer having the structure of

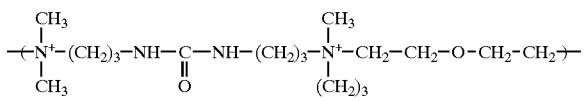

(b) 0 to 1%, more preferably 0.01% to 1.0% of an ethoxylated nonionic surfactant;
(c) 0 to 1%, more preferably 0.01% to 1.0% of an emulsifier;
(d) 0 to 0.75%, more preferably 0.05% to 0.4% of a fragrance or essential oil;
(e) the balance being water, wherein the composition does not contain silver ions, anionic surfactant as crosslinking agent, poly (hexamethylene biguanide) stearate or a cationic surfactant such as a quaternary ammonium compound.

As used herein and in the appended claims the term "perfume" is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight, the essential oils themselves being volatile odoriferous compounds and also serving to dissolve the other components of the perfume.

Suitable essential oils are selected from the group consisting of: Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, White, Camphor powder synthetic technical, Cananga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Coumarin 69° C. (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), Wintergreen, Allocimene, Arbanex™, Arbanol®, Bergamot oils, Camphene, Alpha-Campholenic aldehyde, I-Carvone, Cineoles, Citral, Citronellol Terpenes, Alpha-Citronellol, Citronellyl Acetate, Citronellyl Nitrile, Para-Cymene, Dihydroanethole, Dihydrocarveol, d-Dihydrocarvone, Dihydrolinalool, Dihydromyrcene, Dihydromyrcenol, Dihydromyrcenyl Acetate, Dihydroterpineol, Dimethyloctanal, Dimethyloctanol, Dimethyloctanyl Acetate, Estragole, Ethyl-2 Methylbutyrate, Fenchol, Fernlol™, Florilys™, Geraniol, Geranyl Acetate, Geranyl Nitrile, Glidmint™ Mint oils, Glidox™, Grapefruit oils, trans-2-Hexenal, trans-2-Hexenol, cis-3-Hexenyl Isovalerate, cis-3-Hexanyl-2-methylbutyrate, Hexyl Isovalerate, Hexyl-2-methylbutyrate, Hydroxycitronellal, Ionone, Isobornyl Methylether, Linalool, Linalool Oxide, Linalyl Acetate, Menthane Hydroperoxide, I-Methyl Acetate, Methyl Hexyl Ether, Methyl-2-methylbutyrate, 2-Methylbutyl Isovalerate, Myrcene, Nerol, Neryl Acetate, 3-Octanol, 3-Octyl Acetate, Phenyl Ethyl-2-methylbutyrate, Petitgrain oil, cis-Pinane, Pinane Hydroperoxide, Pinanol, Pine Ester, Pine Needle oils, Pine oil, alpha-Pinene, beta-Pinene, alpha-Pinene Oxide, Plinol, Plinyl Acetate, Pseudo Ionone, Rhodinol, Rhodinyl Acetate, Spice oils, alpha-Terpinene, gamma-Terpinene, Terpinene-4-OL, Terpineol, Terpinolene, Terpinyl Acetate, Tetrahydrolinalool, Tetrahydrolinalyl Acetate, Tetrahydromyrcenol, Tetralol®, Tomato oils, Vitalizair, Zestoral™, HINOKITIOL™ and THUJOPSIS DOLABRATA™.

In the present invention the precise composition of the perfume is of no particular consequence to cleaning performance so long as it meets the criteria of water immiscibility and having a pleasing odor. Naturally, of course, especially for cleaning compositions intended for use in the home, the perfume, as well as all other ingredients, should be cosmetically acceptable, i.e., non-toxic, hypoallergenic, etc.

The water soluble nonionic surfactants utilized in this invention are commercially well known and include the primary aliphatic alcohol ethoxylates, secondary aliphatic alcohol ethoxylates, alkylphenol ethoxylates and ethylene-oxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic surfactant class includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9–15 carbon atoms, such as $C_9$–$C_{11}$ alkanol condensed with 2.5 to 10 moles of ethylene oxide (NEODOL 91-2.5 OR -5 OR -6 OR -8), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl phenol condensed with about 9.5 moles of EO per mole of nonyl phenol, dinonyl phenol condensed with about 12 moles of EO per mole of phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

Also among the satisfactory nonionic surfactants are the water-soluble condensation products of a $C_8$–$C_{20}$ alkanol with a heteric mixture of ethylene oxide and propylene oxide wherein the weight ratio of ethylene oxide to propylene oxide is from 2.5:1 to 4:1, preferably 2.8:1 to 3.3:1, with the total of the ethylene oxide and propylene oxide (including the terminal ethanol or propanol group) being from 60–85%, preferably 70–80%, by weight. Such detergents are commercially available from BASF-Wyandotte and a particularly preferred detergent is a $C_{10}$–$C_{16}$ alkanol condensate with ethylene oxide and propylene oxide, the weight ratio of ethylene oxide to propylene oxide being 3:1 and the total alkoxy content being about 75% by weight.

Condensates of 2 to 30 moles of ethylene oxide with sorbitan mono- and tri-$C_{10}$–$C_{20}$ alkanoic acid esters having a HLB of 8 to 15 also may be employed as the nonionic detergent ingredient in the described composition. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

Other suitable water-soluble nonionic surfactants are marketed under the trade name "Pluronics". The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L 62 and L 64.

Suitable water-soluble non-soap, anionic surfactants used in the instant compositions include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8$–$C_{22}$ alkyl, or acyl group. Such surfactants are employed in the form of water-soluble salts and the salt-forming cation usually is selected from the group consisting of sodium, potassium, ammonium, zinc, magnesium and mono-, di- or tri-$C_2$–$C_3$ alkanolammonium, with the sodium, magnesium and ammonium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

The linear alkyl benzene sulfonate has a high content of 3-(or higher) phenyl isomers and a correspondingly low content (well below 50%) of 2-(or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an a-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735,096.

Examples of satisfactory anionic sulfate surfactants are the preferred $C_8$–$C_{18}$ alkyl sulfate salts and the $C_8$–$C_{18}$ alkyl sulfate salts and the $C_8$–$C_{18}$ alkyl ether polyethenoxy sulfate salts having the formula $R(OC_2H_4)_nOSO_3M$ wherein n is 1 to 12, preferably 1 to 5, and M is a solubilizing cation selected from the group consisting of sodium, potassium, ammonium, zinc, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the alkyl ether polyethenoxy sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. On the other hand, the alkyl ether polyethenoxy sulfates are obtained by sulfating the condensation product of ethylene oxide with a $C_8$–$C_{18}$ alkanol and neutralizing the resultant product. The alkyl ether polyethenoxy sulfates differ from one another in the number of moles of ethylene oxide reacted with one mole of alkanol. Preferred alkyl sulfates and preferred alkyl ether polyethenoxy sulfates contain 10 to 16 carbon atoms in the alkyl group.

The $C_8$–$C_{12}$ alkylphenyl ether polyethenoxy sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic detergents are the $C_9$–$C_{15}$ alkyl ether polyethenoxyl carboxylates having the structural formula $R(OC_2H_4)_nOX$ COOH wherein n is a number from 4 to 12, preferably 5 to 10 and X is selected from the group consisting of $CH_2$, $C(O)R_1$ and

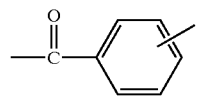

wherein $R_1$ is a $C_1$–$C_3$ alkylene group. Preferred compounds include $C_9$–$C_{11}$ alkyl ether polyethenoxy (7–9) C(O) $CH_2CH_2COOH$, $C_{13}$–$C_{15}$ alkyl ether polyethenoxy (7–9)

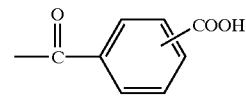

and $C_{10}$–$C_{12}$ alkyl ether polyethenoxy (5–7) $CH_2COOH$. These compounds may be prepared by condensing ethylene oxide with appropriate alkanol and reacting this reaction product with chloracetic acid to make the ether carboxylic acids as shown in U.S. Pat. No. 3,741,911 or with succinic anhydride or phtalic anhydride.

Obviously, these anionic detergents will be present either in acid form or salt form depending upon the pH of the final composition, with the salt forming cation being the same as for the other anionic detergents.

One emulsifier used in the instant composition is LRI manufactured by Wackherr which is a mixture of a PEG-40 hydrogenated Castor oil and PPG-26 buteth 26. Other useful emulsifiers are all the surfactants that can be used to solubilize perfumes or other lipophilic ingredients into water as the surfactants belonging to the following families and showing an HLB higher than 12: the ethoxylated fatty alcohols, ethoxylated lanolin, ethoxylated glycerides or ethoxylated hydroxylated glycerides, ethoxylated amides, ethoxylated carboxylic acids (polyethylene glycol acylates and di-acylates), EO-PO block copolymers or any propoxylated PEO ethers as well as sorbitan and sorbitol esters. More specifically, the following examples can be mentionned:

Ethoxylated castor oil or ethoxylated hydrogenated castor oil as Arlatone 289, 650 and 827 from Imperial Chemical Industries; all mixtures containing ethoxylated castor oil or ethoxylated hydrogenated castor oil as Arlatone 975 and Arlatone 980 from or Imperial Chemical Industries or also the Emulsifier 2/014160 from Dragoco which is a mixture of fatty alcohol polyglycolether and hydrogenated castor oil ethoxylate; all the ethoxylated alkyl alcohol as the range of Brij surfactants from Imperial Chemical Industries or also Arlasolve 200 which is an ethoxylated isohexadecyl alcohol; all the polyethyleneglycol sorbitan mono- and tri- alkanoic acid esters from Imperial Chemical Industries, especially Tween 20 which is polyoxyethylene (20) sorbitan monolaurate.

The final essential ingredient in the inventive compositions having improved interfacial tension properties is water. The proportion of water in the compositions generally is in the range of 20% to 99.5%, preferably 70% to 97% by weight.

In addition to the above-described essential ingredients, the compositions of this invention may often and preferably do contain one or more additional ingredients which serve to improve overall product performance.

The antibacterial solution of this invention may, if desired, also contain other components either to provide additional effect or to make the product more attractive to the consumer. The following are mentioned by way of example: Colors or dyes in amounts up to 0.5% by weight, 2,6-di-tert.butyl-p-cresol, etc., in amounts up to 2% by weight; and pH adjusting agents, such as sulfuric acid, chlorhydric acid or sodium hydroxide, as needed.

All types of organic acid may also be added such as for example lactic, citric, salicylic and glycolic acids for any purpose, as for example for pH adjustment or for improved antibacterial efficacy.

In their final form, the multi purpose liquids are clear or white compositions and should exhibit stability at reduced and increased temperatures. More specifically, such compositions should remain stable in the range of 5° C. to 50° C., especially 10° C. to 43° C. and the compositions exhibit a pH in the range of 3 to 9.

The compositions are directly ready for use as desired and only minimal rinsing is required and substantially no residue or streaks are left behind. Furthermore, because the compositions are free of detergent builders such as alkali metal polyphosphates they are environmentally acceptable and provide a better "shine" on cleaned hard surfaces.

When intended for use in the neat form, the liquid compositions can be packaged under pressure in an aerosol container or in a pump-type sprayer for the so-called spray-and-wipe type of application. The composition can also be dispensed from a non woven or fabric towel which can be used once and discarded or reused several times with adequate rinsing between usage.

The instant formulas explicitly exclude alkali metal silicates and alkali metal builders such as alkali metal polyphosphates, alkali metal carbonates, alkali metal phosphonates and alkali metal citrates because these materials, if used in the instant composition, would cause the composition to have a high pH as well as leaving residue on the surface being cleaned.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

PHMB is reported in literature as being poorly substantive. Adsorption experiments on silica and calcite confirm this information.

Methodology: 100 ml solution of poly (hexamethylene biguanide) hydrochloride (hereinafter referred to as PHMB) at 0.01% in deionized water are put into contact with 30 m$^2$ surface (1.2 g silica at 25 m$^2$/g or 1.5 g calcite at 20 m$^2$/g) for 24 h. The adsorbe PHMB is quantified by the depletion method: the surface is separated from the solution by centrifugation (15 minutes at 3000 rpm) and the non adsorbed polymer is quantified in the supernatant by Total Organic Carbon method (Analytical Department).

| Results: | | |
|---|---|---|
| % Adsorption | On silica | On calcite |
| PHMB at pH = 4 | 24 | 14 |
| PHMB at pH = 7.5 | 42 | 21 |

An increase of the pH slightly improves the "adsorption" of PHMB on both surfaces. This is explained by a decrease of the PHMB solubility (closer to its pK value estimated at about 8–9).

The resistance to rinse of PHMB has also been assessed by ESCA. The conclusion is that the majority of the deposited PHMB on a ceramic tile is easily removed by a first rinsing step.

EXAMPLE 2

The high resistance to rinse of PHMB-SLS system has been demonstrated by colorimetry. Even if a part of the cationic charges is implicated in the complex formation, the high coloration indicates the presence of a high level of PHMB with available cationic charges onto the surface.

Methodology: 50 μl of each solution in deionized water is deposited on a ceramic tile 2.5 cm×2.5 cm. After drying at room temperature, the treated tiles are rinsed with 2×10 ml deionized water. The revelation is then performed with 200 μl Indigotine dye ex. Wackherr (Cl 73015) at 0.033% in deionized water (3 minutes contact). After removing the excess of dye with 10 ml deionized water and drying of the surface, the coloration intensity is measured with a chromameter (Minolta CR200™). The higher the ΔE, the higher the difference of coloration versus the reference tile (no treatment, no contact with the dye). The coloration is the signal of the persistence of the PHMB on the surface after rinsing.

| Results: | |
|---|---|
| | ΔE |
| No treatment | 0.5 |
| SLS 0.1% | 0.5 |
| PHMB 0.2% | 2.0 |
| PHMB 0.2% – SLS 0.1% | 27.0 |

EXAMPLE 3

Illustration of the lasting antibacterial efficacy of the (PHMB-SLS) system versus PHMB alone. Test with wild germs (natural hand's flora)—measure of the surface protection: due to the presence of the SLS, the surface treated with PHMB keeps its protection against germs even after rinsing with 5×10 ml deionized water or after rinsing during 30 seconds under the shower (tap water).

Methodology: Ceramic tiles (2.5 cm×2.5 cm) are treated with 200 μl PHMB 0.2% or (PHMB 0.2% +SLS 0.1 or 0.32%) solution in deionized water or with a solution of a commercially available antibacterial cleaner diluted 4.5× in a way the concentration of PHMB is also 0.2%. After drying of the treatment each tiles are inoculated with 200 μl "hand liquor" in a humid saturated atmosphere. After 5 hours contact, the tiles are rinsed with either 5×10 ml filtered (0.22 μm) tap water or are put during 30 seconds under the shower of tap water (not sterile). The contamination level is determined by direct imprint of the tile on agar plate (Rodac™). The reading (cfu=colony forming units) is performed after 48 h incubation at room temperature.

| Number of cfu 2 replicates | No Rinsing | Tiles rinsed with 5 × 10 ml sterile tap water | Tiles rinsed during 30 seconds under the shower |
|---|---|---|---|
| Not treated tiles | 776/615 | 658/749 | 547/693 |
| Tiles treated with PHMB at 0.2% | 0/0 | 417/297 | 593/376 |
| Tiles treated with PHMB at 0.2% + SLS at 0.1% (ratio PHMB:SLS = 3:1) | 0/0 | 0/0 | 0/0 |
| Tiles treated with PHMB at 0.2% + SLS at 0.32% (ratio PHMB:SLS = 1:1) | 0/0 | 0/0 | Not tested |
| Tiles treated with Dynamo clean bacto diluted 4.5 × (0.2% PHMB + 0.72% dimethyldidecyl ammonium chloride) | 0/0 | 218/141 | 374/318 |

"hand liquor": suspension of germs coming from the natural contamination of human hands.

EXAMPLE 4

The high antibacterial efficiency as well as the resistance to rinse/recontamination of the (PHMB-SLS) treatment on silica surface has also been demonstrated against Staphylococcus aureus.

Methodology: Treatment of the tiles: 150 $\mu$l of the antibacterial solution to test are let dry on 2.5×2.5 cm² ceramic tiles for 1 h 30 in sterile conditions. Rinsing: Tiles are hold with sterile pliers and, using a 10 ml pipette, 2×10 ml sterile tap water are allowed to drain along the tile; let dry for 30 minutes in sterile conditions. Tile inoculation: 50 $\mu$l of inoculum containing $10^5$ to $10^6$ germs (Staphylococcus aureus are let in contact with the tile for either 5 or 17 or 24 hours (time of contact is variable in order to manage 3 inoculations, 2 rinses and plate counting within a period of 4 days); T°=22.5±0.5° C. and RH=63±3%. Germs collection and quantification: Each tile is put in a flask with 20 ml neutralizing DE medium and glass beads; the whole is put under agitation for 10 minutes for extraction of bacterial cells. The resulting solution is diluted and corresponding aliquots are flow in petri dishes with TSA.

| Time scale | Action | Untreated tiles | Tiles treated with (PHMB-SLS) (0.2–0.1% Al, 150 $\mu$l/tile) |
|---|---|---|---|
| t = 0 start | Inoculation with 2 · $10^5$ cfu | | |
| t = 5 hours | Measurement (5 hours contact) before rinsing | 5.90 $10^5$ | Not significant |
| | Measurement after rinsing (2 * ml tap water) | 6.40 $10^2$ | Not significant |
| | Inoculation with 3 · $10^5$ cfu | Not tested | |
| t = 22 hours | Measurement (17 hours contact) before rinsing | 1.09 $10^5$ | 500 |
| | Measurement after rinsing (2 * 10 ml tap water) | 2.85 $10^5$ | Not significant* less 100 |
| | Inoculation with 5 · $10^5$ cfu | | |
| t = 27 hours | Measurement after 5 hours contact | 3.28 $10^5$ | 1.40 $10^5$ |
| t = 51 hours | Measurement after 24 hours contact | 3.25 $10^5$ | Not significant* |

*No significant growth on TSA plates.

EXAMPLE 5

Documentation of the efficiency of (PHMB-SLS) as long lasting antibacterial system in a cleaning composition.

Determination of the long lasting protection of hard surfaces against the germs. Ceramic tiles 2.5×2.5 cm² are treated with 200 $\mu$l of the solutions to test; untreated tiles are used as reference. After drying up to the next day (about 15 hours), a rinsing of the treatment is performed (to evaluate the resistance to rinse of the treatment), either with 5×10 ml deionized water or under the tap water shower during 30 seconds which corresponds to about 150 ml per tile; unrinsed tiles are used as reference. After rinsing, the tiles are let dry for 1 hour. All the tiles (untreated/treated/rinsed/unrinsed) are then inoculated in the horizontal position for 5 hours with 200 $\mu$l of a suspension of wild germs from hand's volunteers (mainly Staphylococcus epidermitis). After gentle rinsing of the surface with 2×10 ml sterile tap water to remove the germs source, the contamination of the surface is determined by direct imprint on Rodac™ agar plates.

| % Al | Fla. 1 | Fla. 2 | Fla. 3 | Fla. 4 | Fla. 5 | Fla. 6 | Fla. 7 |
|---|---|---|---|---|---|---|---|
| PHMB (Vantocil IB) | 0.20 | 0.20 | 0.20 | | 0.20 | 0.20 | 0.20 |
| Sodium lauryl sulfate (Enpicol 0928) | | 0.16 | 0.16 | 0.16 | | 0.16 | 0.16 |
| Dobanol 91-5 | | | 0.10 | 0.10 | 0.10 | | 0.10 |
| LRI emulsifier | | | | | | 0.10 | |
| Fragrance | | 0.05 | 0.05 | 0.05 | 0.05 | 0.05 | 0.05 |
| pH | As is: 3.16 | As is: 3.11 | As is: 3.11 | As is: 9.8 | As is: 3.94 | As is: 3.11 | Adjusted at 6.41 |

Note: fla n° 7 = fla n° 3 with pH adjusted to 6.4.

The antibacterial results expressed as number of cfu (colony forming unit)/tile are:

|  |  | Fla. 1 Untreated Tile | Fla. 1 200 µl/tile | Fla. 2 200 µl/tile | Fla. 3 200 µl/tile | Fla. 4 200 µl/tile | Fla. 5 200 µl/tile | Fla. 6 200 µl/tile | Fla. 6 20 µl/tile | Fla. 7 200 µl/tile |
|---|---|---|---|---|---|---|---|---|---|---|
| The treatment is deposited onto the surface; no rinsing | Repl. 1 | 491 | 1 | 0 | 0 | 83 | 0 | 0 | 0 | 0 |
|  | Repl. 2 | 409 | 0 | 0 | 0 | 78 | 0 | 0 | 0 | 0 |
| The treated tiles are rinsed with 5 × 10 ml deionized water before the contamination | Repl. 1 | 413 | 267 | 2 | 2 | 423 | 184 | 0 | 7 | 1 |
|  | Repl. 2 | 492 | 299 | 0 | 1 | 309 | 324 | 0 | 7 | 7 |
| The treated tiles are rinsed during 30 seconds under a tap water shower before the contamination | Repl. 1 | 352 | nd | nd | 11 | 294 | 203 | 0 | nd | nd |
|  | Repl. 2 | 223 |  |  | 24 | 378 | 382 | 0 |  |  |

Nd: not determined

If the treatments are not rinsed before the contamination with the wild germs all the compositions containing PHMB protect the surface from the contamination (fla n°1, 2, 3, 5, 6, 7). The blend: SLS 0.16%/Dobanol 91-5 0.10%/fragrance 0.05% (fla n°4) has a slight effect against the germs (about 80 cfu versus about 450 for the untreated tiles) but is much more less efficient than compositions with PHMB.

If the treatments are rinsed with 5×10 ml deionized water before the contamination with the wild germs the treatment with PHMB alone is not able anymore to protect the surface. The PHMB has been removed during the rinsing (fla n°1). If the PHMB is combined with a small level of SLS, the surface remains protected even after the rinsing of the treatment. The SLS makes the PHMB substantive (fla n°2). It is also observed once the (PHMB-SLS) system is incorporated in a perfumed composition containing Dobanol 91-5 as wetting agent (fla n°3). If the PHMB is removed from this composition n°3 (leading to fla n°4) or if SLS is removed (leading to fla n°5), the protection of the surface is no more effective. This demonstrates that it is the (PHMB-SLS) system that is the active substantive antibacterial agent. The finished perfumed cleaning composition with LRI emulsifier (fla n°6) also ensure a very good protection of the surface. It is still effective if the quantity of the treatment is reduced by a factor 10 (20 µl/tile i.o. 200 µl/2.5×2.5 cm² tile). The (PHMB-SLS) system is efficient at both pH 3–3.5 and pH 6.4 (fla n°3 and 7).

If the treatment is rinsed during 30 seconds under tap water. Confirmation of previous results: both components PHMB and SLS have to be present concomitantly to ensure a long lasting germ protection of the surface. The 2 complete compositions (fla n°3 and 6) with this active system are efficient to ensure a long lasting protection of the ceramic surface against the germs, with a slightly better result for fla n°6 based on LRI emulsifier.

Fla n°3 which is PHMB 0.2%/SLS 0.16%/Dobanol 91-5 0.1%/fragrance 0.05% and Fla n°6 which is PHMB 0.2%/SLS 0.16%/LRI 0.1%/fragrance 0.05% are effective compositions for a long lasting protection of surfaces against the germ contamination.

EXAMPLE 6

Applicability of the (cationic polymer-SLS) antibacterial complex exclusion to other anionic surfactants. Methodology: Lasting antibacterial protection of the surface and intrinsic antibacterial efficacy: Ceramic tiles 2.5×2.5 cm² are treated with 200 µl of the solutions to test; untreated tiles are used as reference. After drying of the treatment for about 15 hours, the treated surface is rinsed either with 5×10 ml deionized water (pipette) or under the tap water shower during 30 seconds (which corresponds to about 150 ml per tile) and let dry for 1 hour. Unrinsed tiles are used to determine the intrinsic antibacterial efficacy of the treatment. All the tiles (untreated/treated/rinsed/unrinsed) are inoculated in the horizontal position for 5 hours with 200 µl of a suspension of wild germs from hand's volunteers (mainly Staphylococcus epidermitis). After gentle rinsing of the surface with 2×10 ml sterile tap water to remove the non-adhering germs, the contamination on the surface is determined by direct imprint on Rodac™ nutrient agar plate. The 'Colony Forming Units' are counted under a microscope (40×magnification) after 48 h. incubation at room temperature. A check is performed after 24 h. additional incubation at 30° C.

|  |  | Intrinsic efficiency of the composition - No rinsing of the treatment applied onto the ceramic tiles (number of cfu*/tile) | | Resistance to rinse of the antibacterial treatment - rinsing of the treatment with 5 × 10 ml deionized water (number of cfu*/tile) | |
|---|---|---|---|---|---|
| Composition | pH | Repl. 1 | Repl. 2 | Repl. 1 | Repl. 2 |
| Untreated tile |  | 170 | 160 | 148 | 111 |
| PHMB 0.2% | 3.09 | 1 | 15 | 40 | 160 |
| PHMB 0.2% + SLS 0.2% | 3.09 | 0 | 0 | 1 | 0 |
| PHMB 0.2% + SLES 0.2% | 3.00 | 0 | 0 | 3 | 2 |
| PHMB 0.2% + LAS 0.2% | 2.97 | 0 | 1 | 16 | 27 |

As often previously observed, the antibacterial protection of the surface brought by the PHMB alone does not sustain rinsing: the contamination level of the surface increases as the treatment is rinsed. Once combined with a low level of SLS, the antibacterial protection of the surface is maintained even after the rinsing of the treatment.

The same benefit is observed with other anionic surfactants as the SLES or the LAS. The lasting antibacterial efficacy (after rinsing) obtained with the PHMB-LAS system is lower than with the SLS or SLES surfactants, but remains better than with the PHMB alone.

EXAMPLE 7

Applicability of the (PHMB-anionic surfactant) antibacterial complex exclusion principle to another cationic antibacterial polymer: Mirapol A15.

The purpose of this experiment is to determine if the principle of delivering a lasting antibacterial efficacy onto hard surfaces by combining a low level of anionic surfactant with the PHMB can also be applied to other cationic polymer with antibacterial properties. We made the trial with the Mirapol A15, a cationic polymer from Rhodia. The main difference between the Mirapol A15 and the PHMB is that the Mirapol A15 is a quaternized polymer with a permanent cationic charge, whereas the PHMB bears a delocalized cationic charge which density is dependent on the pH.

Methodology: Same as Example 6.

| Composition | pH | Intrinsic efficiency of the composition - No rinsing of the treatment applied onto the ceramic tiles (number of cfu*/tile) | | Resistance to rinse of the antibacterial treatment - rinsing of the treatment with 5 × 10 ml deionized water (number of cfu*/tile) | |
|---|---|---|---|---|---|
| | | Repl. 1 | Repl. 2 | Repl. 1 | Repl. 2 |
| Untreated tile | | 170 | 160 | 148 | 111 |
| PHMB 0.2% | 3.09 | 1 | 15 | 40 | 160 |
| PHMB 0.2% + SLS 0.2% | 3.09 | 0 | 0 | 1 | 0 |
| Mirapol A15 0.2% | 7.29 | 22 | 29 | 171 | 142 |
| Mirapol A15 0.2% + SLS 0.1% | 8.51 | 7 | 7 | 19 | 20 |
| Mirapol A15 0.2% + SLS 0.2% | 9.23 | 4 | 1 | 1 | 2 |

The exclusion principle can also be applied to other cationic polymers for a lasting antibacterial protection of hard surfaces. In presence of SLS, the antibacterial protection of the surface brought by the Mirapol A15 is maintained even after rinsing of the treatment with 50 ml deionized water. The lasting antibacterial protection is better in presence of 0.2% SLS than with 0.1% SLS (for 0.2% Mirapol A15).

What is claimed:

1. An aqueous antibacterial solution which comprises approximately by weight:

(a) a complex of 0.01% to 5.0% of an anionic surfactant and 0.01% to 2% of a cationic polymer selected from the group consisting of poly (hexamethylene biguanide) hydrochloride having the structure of:

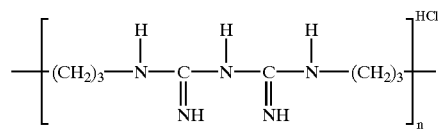

where the average n=4 to 6 and a quaternized cationic polymer having the structure of

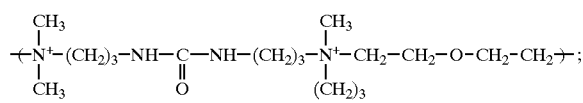

(b) 0.01% to 1.0% of an ethoxylated nonionic surfactant;

(c) 0.01% to 1.0% of an emulsifier selected from the group consisting of ethoxylated hydrogenated castor oil, PPG-26 buteth26, ethoxylated lanolin, ethoxylated glycerides, ethoxylated hydroxylated glycerides, ethoxylated amides, ethoxylated carboxylic acids and ethoxylated castor oil and mixtures thereof;

(d) 0.05% to 0.4% of a fragrance or essential oil;

(e) the balance being water, wherein the composition does not contain silver ions, anionic surfactant as crosslinking agent, poly (hexamethylene biguanide) stearate or a cationic surfactant such as a quaternary ammonium compound.

2. The composition of claim 1 wherein said emulsifier contains ethoxylated castor oil or ethoxylated hydroxylated castor oil.

* * * * *